United States Patent
Hashimoto et al.

(10) Patent No.: US 8,445,516 B2
(45) Date of Patent: May 21, 2013

(54) PHARMACEUTICAL COMPOSITION FOR PROMOTING ANGIOGENESIS

(75) Inventors: Ayako Hashimoto, Tokushima (JP); Takashi Imaizumi, Naruto (JP); Goro Miyakoda, Matsushige (JP); Toyoki Mori, Naruto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1519 days.

(21) Appl. No.: 10/587,045

(22) PCT Filed: Jan. 26, 2005

(86) PCT No.: PCT/JP2005/001444
§ 371 (c)(1),
(2), (4) Date: Jul. 24, 2006

(87) PCT Pub. No.: WO2005/072734
PCT Pub. Date: Aug. 11, 2005

(65) Prior Publication Data
US 2009/0187025 A1    Jul. 23, 2009

(30) Foreign Application Priority Data
Jan. 29, 2004  (JP) ................................. 2004-020859

(51) Int. Cl.
*A61K 31/4468*  (2006.01)

(52) U.S. Cl.
USPC .......................................... 514/329; 546/223

(58) Field of Classification Search
USPC .......................................... 514/329; 546/223
See application file for complete search history.

(56) References Cited

U.S. PATENT DOCUMENTS

| | | |
|---|---|---|
| 3,063,996 A | 11/1962 | Gordon |
| 3,454,566 A | 7/1969 | Lindenmann et al. |
| 3,875,165 A | 4/1975 | Archibald et al. |
| 4,454,130 A | 6/1984 | Tominaga et al. |
| 4,455,422 A | 6/1984 | Banno et al. |
| 4,460,593 A | 7/1984 | Banno et al. |
| 4,468,402 A | 8/1984 | Tominaga et al. |
| 4,487,772 A | 12/1984 | Tominaga et al. |
| 4,514,398 A | 4/1985 | Regnier et al. |
| 4,567,187 A | 1/1986 | Banno et al. |
| 4,619,932 A | 10/1986 | Banno et al. |
| 4,882,329 A | 11/1989 | Lerch et al. |
| 4,886,809 A | 12/1989 | Tamada et al. |
| 4,895,841 A | 1/1990 | Sugimoto et al. |
| 5,008,274 A | 4/1991 | Nishi et al. |
| 5,071,856 A | 12/1991 | Tamada et al. |
| 5,100,901 A | 3/1992 | Sugimoto et al. |
| RE33,906 E | 4/1992 | Vecchietti et al. |
| 5,189,045 A | 2/1993 | Peglion et al. |
| 5,260,318 A | 11/1993 | Lubisch et al. |
| 5,310,743 A | 5/1994 | Schilling et al. |
| 5,356,904 A | 10/1994 | Freidinger et al. |
| 5,656,642 A | 8/1997 | Fujioka et al. |

FOREIGN PATENT DOCUMENTS

| | | |
|---|---|---|
| CA | 2011834 | 9/1990 |
| CH | 535 767 | 5/1973 |
| DE | 2034640 | 2/1971 |
| DE | 2311570 | 9/1973 |
| DE | 3529994 | 2/1987 |
| DE | 3907974 | 9/1990 |
| EP | 0 000 355 | 1/1979 |
| EP | 0 001 175 | 3/1979 |
| EP | 0 090 733 | 10/1983 |
| EP | 0 097 000 | 12/1983 |
| EP | 0 099 139 | 1/1984 |
| EP | 0 144 101 | 6/1985 |
| EP | 0 156 433 | 10/1985 |
| EP | 0 191 603 | 8/1986 |
| EP | 0 255 134 | 2/1988 |
| EP | 0 296 560 | 12/1988 |
| EP | 0 297 661 | 1/1989 |
| EP | 0 318 029 | 5/1989 |
| EP | 0 344 577 | 12/1989 |
| EP | 0 457 686 | 11/1991 |
| EP | 0 481 299 | 4/1992 |

(Continued)

OTHER PUBLICATIONS oOrito et al. "Mechanisms of action . . . " J. Pharmcol. and Exp. Ther. vo. 231 (2) p. 604-611 (1999).*

(Continued)

*Primary Examiner* — Celia Chang
(74) *Attorney, Agent, or Firm* — Finnegan, Henderson, Farabow, Garrett & Dunner, L.L.P.

(57) ABSTRACT

The present invention provides a pharmaceutical composition for promoting angiogenesis, which has an angiogenesis promoting action even in a vascular culturing system without effect of microcirculation. A pharmaceutical composition for promoting angiogenesis of the present invention comprises at least one compound selected from a group consisting of a piperidine compound represented by the general formula (1) or salts thereof: (wherein R represents a benzoyl group which may have, as substituents on the phenyl ring, 1 to 3 groups selected from a group consisting of an amino group, which may have a lower alkanoyl group, and a lower alkyl group; $R^1$ represents a hydrogen atom or a lower alkyl group; and $R^2$ represents a phenyl lower alkyl group).

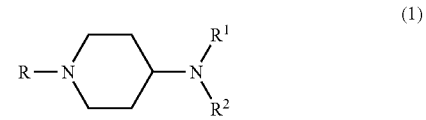

(1)

4 Claims, No Drawings

FOREIGN PATENT DOCUMENTS

| | | |
|---|---|---|
| EP | 0 532 456 | 3/1993 |
| GB | 1 268 469 | 3/1972 |
| GB | 2 216 516 A | 10/1989 |
| JP | 41-19506 | 11/1966 |
| JP | 43-29585 | 12/1968 |
| JP | 44-17387 | 7/1969 |
| JP | 49-273 | 1/1974 |
| JP | 51-65770 | 6/1976 |
| JP | 51-68574 | 6/1976 |
| JP | 51-118771 | 10/1976 |
| JP | 52-282 | 1/1977 |
| JP | 52-283 | 1/1977 |
| JP | 52-83380 | 7/1977 |
| JP | 52-118474 | 10/1977 |
| JP | 54-16478 | 2/1979 |
| JP | 54-36259 | 3/1979 |
| JP | 54-92974 | 7/1979 |
| JP | 55-85520 | 6/1980 |
| JP | 56-92884 | 7/1981 |
| JP | 56-125385 | 10/1981 |
| JP | 56-161386 | 12/1981 |
| JP | 56-164183 | 12/1981 |
| JP | 56-164184 | 12/1981 |
| JP | 56-166188 | 12/1981 |
| JP | 57-40482 | 3/1982 |
| JP | 57-154129 | 9/1982 |
| JP | 57-171974 | 10/1982 |
| JP | 57-192383 | 11/1982 |
| JP | 59-5160 | 1/1984 |
| JP | 59-21680 | 2/1984 |
| JP | 60-149583 | 8/1985 |
| JP | 60-226862 | 11/1985 |
| JP | 61-161262 | 7/1986 |
| JP | 61-183283 | 8/1986 |
| JP | 62-48665 | 3/1987 |
| JP | 62-89679 | 4/1987 |
| JP | 63-150237 | 6/1988 |
| JP | 63-170311 | 7/1988 |
| JP | 64-61468 | 3/1989 |
| JP | 64-79151 | 3/1989 |
| JP | 1-316356 | 12/1989 |
| JP | 2-138161 | 5/1990 |
| JP | 2-169569 | 6/1990 |
| JP | 2-306951 | 12/1990 |
| JP | 4-282366 | 10/1992 |
| JP | 7-188021 | 7/1995 |
| SA | 671 679 | 3/1967 |
| TW | 125198 | 12/1989 |
| WO | WO 94/22826 | 10/1994 |

OTHER PUBLICATIONS

Azevedo et al. "Vascular enthothelial . . . " Biochem. Biophy. Res. Comm. v.297, p. 1270-1276 (2002).*
Zhou et al. "Internal division of . . . " Cell Tiss. Res. vo.293, p. 293-303 (1998).*
Sumi et al. "OPC-28326 . . . " Biomed. Pharm. v. 61, p. 209-215 (2007).*
Freidinger et al. "Carbostyril . . . " CA122;105695 (1995).*
Nakanishi et al. "Piperidine . . . " CA 66:46341 (1967.*
Olofson et al. "Test of . . . " CA101:54884 (1984).*
Cecil "medical textbook" p. 247(1983).*
Stroke Wikipedia (from internet) p. 1-22 (2011).*
Tominaga, "Peripheral Vessel Dilator Containing Piperidine Derivative as Active Component and New Piperidine Derivative", Patent Abstracts of Japan of JP-A-6-340627, (1995).
Sun, et al., "OPC-28326, a Selective Femoral Vasodilator, Is an alpha$_{2C}$-Adrenoceptor-Selective Antagonist", Journal of Pharmacology and Experimental Therapeutics, vol. 299, No. 2, XP-002325918, pp. 652-658, (2001).
Ware, et al., "Angiogenesis in ischemic heart disease", Nature Medicine, Nature Publishing, vol. 3, No. 2, XP-002074058, pp. 158-164, (Feb. 1997).
Imaizumi, et al., "OPC-28326, a Selective Peripheral Vasodilator, Possesses an Angiogenic Property", Journal of Pharmacological Sciences, vol. 94, no. Supplement 1, p. 155P, XP009046812, (Mar. 8-10, 2004).
Hashimoto, et al., "OPC-28326, a Selective Peripheral Vasodilator, Possesses a Stabilizing Effect on Newly Formed Microvessels", Journal of Pharmacological Sciences, vol. 94, no. Supplement 1, p. 156P, XP009046811, (Mar. 8-10, 2004).
Avasthi, K. et al., "Synthesis and Reactions of 3-AZA-7-Oxabicyclo[4.1.0] Heptanes With Nitrogen and Sulfur Nucleophiles", Can. J. Pharm. Sci., 16:52-56 (1981).
Backstrom et al., "Preparation of Pyrocatechol Derivatives For Treating Parkinson's Disease," CA 109:128570x (1988).
CAPLUS Registry RN 116330-61-1, (1988).
Caroon, J. M. et al., "Antihypertensive 1-Acyl-4-[2-(1,4-benzodioxan-2-yl)-2-hydroxyethylamino] piperidines$^1$", J. Pharma. Sci., 76:32-34 (1987).
Lampe, J. W. et al., "Cardiotonic Agents. 6. Histamine Analogues as Potential Cardiovascular Selective H$_2$ Agonists", J. Med. Chem., 33:1688-1697 (1990).
Mai, K. et al., "A Fast N-Substituted α-Aminonitrile Synthesis", Synthetic Comm., 15:157-163 (1985).
Mattson, R.J. et al., "An Improved Method for Reductive Alkylation of Amines Using Titanium(IV) Isopropoxide and Sodium Cyanoborohydride", J. Org. Chem., 55:2552-2554 (1990).
Obase, H. et al., "Synthesis of (1-Substituted Piperidin-4-yl)-1H-benzimidazoles and (1-Substituted Piperidin-4-yl)-3,4-dihydroquinazolines as Possible Antihypertensive Agents", J. Heterocyclic Chem., 20:565-573 (1983).
Olofson, R. A. et al., "Tests of a Piperidino Mask for the Protection of Functionalized Carbon Sites in Multistep Syntheses", J. Org. Chem., 49:2795-2799 (1984).
Takai, H. et al., "Synthesis of 1- and 3-(1-Substituted 4-Piperidinyl)-1,2,3,4-tetrahydro-2-oxoquinazolines as Potential Antihypertensive Agents", Chem. Pharm. Bull., 33:1116-1128 (1985).
Freedman, S.B. et al., "Therapeutic Angiogenesis for Ischemic Cardiovascular Disease," J. Mol. Cell Cardiol. 33: 379-93 (2001).
Gowda, R.M. et al., "Reversible Myocardial Dysfunction: Basics and Evaluation," Int. J. Cardiol. 97: 349-53 (2004).
Keledjian, K. and Kyprianou, N., "Anoikis Induction by Quinazoline Based α1 Adrenoceptor Antagonists in Prostate Cancer Cells: Antagonistic Effect of BCL-2," J. Urology 169: 1150-56 (2003).
Orito, K. et al., "α2-Adrenoceptor Antagonist Properties of OPC-28326, a Novel Selective Peripheral Vasodilator," Brit. J. Pharmacol. 134: 763-70 (2001).
Pan, S.L. et al., "Identification of Apoptotic and Antiangiogenic Activities of Terazosin in Human Prostate Cancer and Endothelial Cells," J. Urology 169: 724-29 (2003).
Sasayama, S. et al., "Recent Insights Into Coronary Collateral Circulation," J. Am. Heart Assoc. 85: 1197-204 (1992).
Ye, L. et al., "Angiopoietin-1 for Myocardial Angiogenesis: A Comparison Between Delivery Strategies," Eur. J. Heart Failure 9: 458-65 (2007).

* cited by examiner

PHARMACEUTICAL COMPOSITION FOR PROMOTING ANGIOGENESIS

TECHNICAL FIELD

The present invention relates to a pharmaceutical composition for promoting angiogenesis.

BACKGROUND ART

Angiogenesis is a process for formation of a systemic vascular network initiating from embryonic stage, and is related to generation via complex processes including not only proliferation of vascular endothelial cells but also migration of endothelial cells or tube formation, formation of basement membrane, etc.

Recently, studies on factors regulating angiogenesis have been progressed, and therapeutic application thereof has been attempted. Development of tumors and the like profoundly relates to dysregulated angiogenesis. Treatment thereof requires suppression of angiogenesis, however, on the contrary, therapy for promoting angiogenesis has also been required widely.

For example, factors for promoting angiogenesis, vascular endothelial growth factor (VEGF), basic fibroblast growth factor (bFBF), hepatocyte growth factor (HGF), and the like have been found, and by utilizing these growth factors and genes thereof, therapeutic methods for the diseases essentially requiring improvement of blood circulation, such as arteriosclerosis obliterans, ischemic heart disease, and the like, have been attempted and examined.

However, since these growth factors are proteins, there are many problems such as difficulty with the oral administration, an anaphylactic reaction caused by repeated administration, safety of virus in case of gene therapy using a viral vector and adverse side reactions like edematous, and accordingly new development of therapeutic agents are desired.

Physiological angiogenesis is recognized in microvascular formation of mature tissues and is known to be generated by such a physical factor as change in intravascular pressure. It has been reported, for example, that long-term administration of prazosin or adenosine having vasodilating activity increases physical shear stress to blood vessels in microcirculation and thus promotes angiogenesis (Dawson, J. M., Cardiovasc. Res. 23, 913-920, 1989; and Ziada, A. M., Cardiovasc. Res. 18, 724-732, 1984), however, these compounds have no direct angiogenesis promoting action.

DISCLOSURE OF THE INVENTION

The present invention aims at providing drugs having direct angiogenesis promoting action in order to overcome the above-described problems.

The present inventors have extensively studied to find out novel drugs having direct angiogenesis promoting action. As a result, we have found that a piperidine compound represented by the following general formula (1) or salts thereof have direct angiogenesis promoting action as well as promotion of vascular endothelial cell migration and tube formation even in an aortic ring culturing assay which was considered not to reflect the vasodilating action. The present invention has been completed according to such knowledge.

1. The present invention provides a pharmaceutical composition for promoting angiogenesis, comprising at least one compound selected from a group consisting of a piperidine compound represented by the general formula (1) or salts thereof:

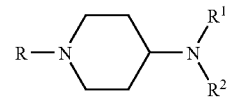

wherein R represents a benzoyl group which may have, as substituents on the phenyl ring, 1 to 3 groups selected from a group consisting of an amino group, which may have a lower alkanoyl group, and a lower alkyl group; $R^1$ represents a hydrogen atom or a lower alkyl group; and $R^2$ represents a phenyl lower alkyl group.

2. The present invention provides a pharmaceutical composition for promoting angiogenesis, as is mentioned above, wherein a piperidine compound is 4-[N-methyl-N-(2-phenylethyl)amino]-1-(3,5-dimethyl-4-propionylaminobenzoyl)piperidine.

3. The present invention provides a pharmaceutical composition for promoting angiogenesis, as is mentioned above, wherein the pharmaceutical composition for promoting angiogenesis is a preventive or therapeutic drug for diseases with insufficient development and regeneration of blood vessels, and various diseases caused by ischemia.

4. The present invention provides a pharmaceutical composition for promoting angiogenesis, as is mentioned above, wherein the diseases with insufficient development and regeneration of blood vessels, and various diseases caused by ischemia are myocardial infarction, angina pectoris, cerebral infarction, senile dementia and various organ damages accompanied by diabetes mellitus.

A piperidine compound of the general formula (1) or salts thereof contained in a pharmaceutical composition for promoting angiogenesis of the present invention is a known compound such as described in JP-A-6-340627 (1994).

In the present invention, each group shown in the general formula (1) hereinabove will be described more specifically as follows.

As a lower alkyl group, examples thereof include a linear or branched alkyl group having 1 to 6 carbon atoms, such as methyl group, ethyl group, n-propyl group, isopropyl group, n-butyl group, isobutyl group, tert-butyl group, sec-butyl group, n-pentyl group, neopentyl group, n-hexyl group, isohexyl group, 3-methylpentyl group, etc.

As an amino group which may have a lower alkanoyl group, examples thereof include an amino group, which may have a linear or branched alkanoyl group having 1 to 6 carbon atoms, such as amino group, formylamino group, acetylamino group, propionylamino group, butyrylamino group, isobutyrylamino group, pentanoylamino group, tert-butylcarbonylamino group, hexanoylamino group, etc.

As a benzoyl group which may have 1 to 3 substituents on the phenyl ring, selected from a group consisting of an amino group which may have a lower alkanoyl group, and a lower alkyl group, examples thereof include a benzoyl group, which may have 1 to 3 substituents on the phenyl ring, selected from a group consisting of an amino group which may have a linear or branched alkanoyl group having 1 to 6 carbon atoms, and a linear or branched alkyl group having 1 to 6 carbon atoms, such as benzoyl group, 2-methylbenzoyl group, 3-ethylbenzoyl group, 4-n-propylbenzoyl group, 2-isopropylbenzoyl group, 3-n-butylbenzoyl group, 4-isobutylbenzoyl group, 2-tert-butylbenzoyl group, 3-sec-butylbenzoyl group, 4-n-pentylbenzoyl group, 2-neopentylbenzoyl group, 3-n-hexylbenzoyl group, 4-isohexylbenzoyl group, 2-(3-methylpentyl)benzoyl group, 2,3-dimethylbenzoyl group, 2,4,6-trimethylbenzoyl group, 2-aminobenzoyl group, 3-formylaminobenzoyl group, 4-acetylaminobenzoyl group, 2-propionylaminobenzoyl group, 3-butyrylaminobenzoyl group, 4-isobutyrylaminobenzoyl group, 2-pentanoylaminobenzoyl group, 3-tert-butylcarbonylaminobenzoyl group, 4-hexanoylaminobenzoyl group, 2,4-diacetylaminobenzoyl group, 2,3,4-triacetylaminobenzoyl group, 3,5-dimethyl-4-propionylaminobenzoyl group, etc.

As a phenyl lower alkyl group, examples thereof include a phenyl alkyl group whose alkyl moiety is a linear or branched alkyl group having 1 to 6 carbon atoms, such as benzyl group, 1-phenylethyl group, 2-phenylethyl group, 3-phenylpropyl group, 4-phenylbutyl group, 5-phenylpentyl group, 6-phenylhexyl group, 1,1-dimethyl-2-phenylethyl group, 2-methyl-3-phenylpropyl group, etc.

Among a piperidine compound represented by the general formula (1) of the present invention, a compound having a basic group can easily form a salt with a general pharmacologically acceptable acid. As such an acid includes, for example, an inorganic acid such as sulfuric acid, nitric acid, hydrochloric acid, phosphoric acid, hydrobromic acid, etc.; and an organic acid such as acetic acid, p-toluene sulfonic acid, ethane sulfonic acid, oxalic acid, maleic acid, fumaric aid, malic acid, tartaric acid, citric acid, succinic acid, benzoic acid, etc.

Among a piperidine compound represented by the general formula (1) of the present invention, a compound having an acidic group can easily form a salt by reacting with a pharmaceutically acceptable basic compound. An example of such a basic compound includes sodium hydroxide, potassium hydroxide, calcium hydroxide, sodium carbonate, potassium carbonate, sodium hydrogen carbonate, potassium hydrogen carbonate, etc.

A piperidine compound of the present invention includes an optical isomer.

A piperidine compound of the general formula (1) or a salt thereof is usually used in a form of the general pharmaceutical preparation. The preparation is produced by using commonly used diluents or excipients such as fillers, binders, wetting agents, disintegrators, surface active agents, lubricants, etc. Various forms of pharmaceutical preparations can be selected depending on therapeutic objectives, and representative examples include tablets, pills, powders, liquids and solutions, suspensions, emulsions, granules, capsules, suppositories, injections (liquids, suspensions, etc.), ointments, etc.

For shaping tablet form, such a carrier can be used, for example, excipients such as lactose, saccharose, sodium chloride, glucose, urea, starch, calcium carbonate, kaolin, crystalline cellulose, silicate, etc.; binders such as water, ethanol, propanol, simple syrup, glucose solution, starch solution, gelatin solution, carboxymethylcellulose, shellac, methylcellulose, potassium phosphate, polyvinylpyrrolidone, etc; disintegrators such as dried starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, etc.; disintegration suppressants such as saccharose, stearin, cacao butter, hydrogenated oil, etc.; absorption enhancers such as quaternary ammonium base, sodium lauryl sulfate, etc.; moisturizing agents such as glycerine, starch, etc.; adsorbents such as starch, lactose, kaolin, bentonite, colloidal silicate, etc.; lubricants such as refined talc, stearic acid salt, borate powder, polyethylene glycol, etc. Further, tablets can optionally be prepared in tablet form coated with conventional coating such as sugar-coated tablets, gelatin encapsulated tablets, enteric coated tablets and film coated tablets, or double layered tablets and multilayered tablets.

For shaping pill form, such a carrier can be used, for example, excipients such as glucose, lactose, starch, cacao butter, hydrogenated vegetable oil, kaolin, talc, etc.; binders such as gum arabic powder, tragacanth gum powder, gelatin, ethanol, etc.; disintegrators such as laminaran, agar, etc.

For shaping suppository form, such a carrier can be used, for example, polyethylene glycol, cacao butter, higher alcohols, esters of higher alcohols, gelatin, semisynthetic glyceride, etc.

Capsules can be prepared by filling a compound of the present invention by mixing with the above exemplified various carriers into hard gelatin capsules or soft capsules according to conventional capsulation means.

For preparing injection, liquids and solutions, emulsions and suspensions are sterilized, and are preferably isotonic to blood. For shaping such forms, such a diluent can be used, for example, water, ethyl alcohol, macrogol, propylene glycol, ethoxylated isostearyl alcohol, polyoxylated isostearyl alcohol, polyoxyethylene sorbitan fatty acid esters, etc.

Sufficient amount of sodium chloride, glucose or glycerol for preparing an isotonic solution can also be admixed in the pharmaceutical preparations, and further conventional solubilizing agents, buffers, soothing agents, and the like can also be added.

If necessary, coloring agents, preservatives, aromatics, flavors, sweeteners, and the like and other drugs can also be added in the pharmaceutical preparation.

For shaping paste, cream and gel form, such a diluent can be used, for example, white petrolatum, paraffin, glycerin, cellulose derivative, polyethylene glycol, silicon, bentonite, etc.

An amount of a compound of the present invention which should be contained in the pharmaceutical preparation of the present invention is not especially limited and is selected adequately in a broad range, generally at about 1-70% by weight, preferably 1-30% by weight in the pharmaceutical preparation.

A method for administration of the above pharmaceutical preparation is not especially limited, and is determined depending on various preparation forms, patient age, sex and other conditions and disease severity. For example, tablets, pills, liquids and solutions, suspensions, emulsions, granules and capsules are administered orally. Injections are administered intravenously alone or admixed with conventional fluid replacement such as glucose, amino acids, etc., and, if necessary, are administered alone intramuscularly, intracutaneously, subcutaneously or intraperitoneally. Suppositories are administered intrarectally.

Dosage of the above pharmaceutical preparation is selected depending on direction for use, patient age, sex and other conditions and disease severity, and an amount of the compound of the general formula (1) as an active ingredient is generally about 0.01-10 mg/kg/day. The active ingredient is preferably contained at 0.1-200 mg in a unit dosage form.

A pharmaceutical composition for promoting angiogenesis of the present invention is useful as a preventive or therapeutic drug for diseases with insufficient development and regeneration of blood vessels, and further various diseases caused by ischemia such as myocardial infarction, angina pectoris, cerebral infarction, senile dementia, various organ damage accompanied by diabetes mellitus, etc.

BEST MODE FOR CARRYING OUT THE INVENTION

The present invention will be more clearly explained by referring to Examples of preparations and pharmacological tests as follows.

PREPARATION EXAMPLE 1

4-[N-methyl-N-(2-phenylethyl)amino]-1-(3,5-dimethyl-4-propionylaminobenzoyl)piperidine (5 mg), starch (132 mg), magnesium stearate (18 mg) and lactose (45 mg) were mixed, and tableted by conventional means to produce tablets containing the above described amount of components in a tablet.

PREPARATION EXAMPLE 2

Methylparaben (0.18 g), propylparaben (0.02 g), sodium metabisulfite (0.1 g) and sodium chloride (0.9 g) were dissolved in adequate amount of distilled water for injection at 80° C. under stirring. Thus obtained solution was cooled to 40° C., and 4-[N-methyl-N-(2-phenylethyl)amino]-1-(3,5-dimethyl-4-propionylaminobenzoyl)piperidine (500 mg), polyethylene glycol (molecular weight=4000, 0.3 g) and polyoxyethylene sorbitan monooleate (0.4 g) were gradually dissolved therein, then distilled water for injection was added to the solution to prepare final volume (100 ml). The solution was sterilized by being aseptically filtered with a proper filter paper, and separately dispensed each 1 ml into an ampule to prepare injections.

In pharmacological tests hereinbelow, 4-[N-methyl-N-(2-phenylethyl)amino]-1-(3,5-dimethyl-4-propionylaminobenzoyl)piperidine (hereinbelow this compound is designated as "Test Compound A") is used as a test compound.

PHARMACOLOGICAL TEST EXAMPLE 1

Angiogenesis Promoting Action of Test Compound A

The test was conducted according to a report by Nicosia R. F. et al. (In Vitro Cell Dev Biol 26, 119-128, 1990). Briefly, thoracic aorta was removed from rat under ether anesthesia, and aortic rings were obtained by cross-sectioning at 1 mm intervals. The aortic rings were embedded into type I collagen gel (Koken Co.). Further, MCDB131 medium (Gibco BRL Co.) containing the Test Compound A was added to the upper layer, and the medium was exchanged every three days. After 7 days from the culture, micro-vessels newly grown from a cutting section of the aortic ring specimens were stained with alkaline phosphatase, then numbers of micro-vessels observed based on digital camera image were counted by using Scion Image (Scion Corp.). The statistical analysis was performed as follows: Data were analyzed using Dunnett's test with randamized block design. The difference between test compound groups and non-treated group were considered statistical significant at $P<0.05$.

The results are shown in Table 1. As is shown in Table 1, the Test Compound A indicated significantly increased numbers of newly grown micro-vessels with dose dependent manner in the thoracic aortic ring specimens of rat, as compared with those of a non-treated control group. Accordingly, the Test Compound A was clearly demonstrated to have angiogenesis promoting action.

TABLE 1

|  | Concentration (−Log M) | Number | Number of micro-vessels |
|---|---|---|---|
| Control |  | 6 | 20 ± 2 |
| Test Compound A | 12 | 7 | 24 ± 3 |
|  | 11 | 7 | 22 ± 3 |
|  | 10 | 7 | 30 ± 3 * |
|  | 9 | 7 | 27 ± 2 |
|  | 8 | 7 | 32 ± 4 * |
|  | 7 | 7 | 33 ± 3 * |
|  | 6 | 6 | 35 ± 4 * |

Values were expressed as the mean ± SE
** $P < 0.05$ vs. control

PHARMACOLOGICAL TEST EXAMPLE 2

Effect of Test Compound A on Vascular Endothelial Cell Migration

The test was conducted according to a report by Witzenbichler, B. et al. (J. Biol. Chem., 273, 18514-18521, 1998). Briefly, human aortic endothelial cells (Cambrex Corp.) were cultured in MCDB131 medium to confluent state. Cell migration was tested by using a 48 well micro chemotaxis chamber (Neuro Probe Inc.). The Test Compound A was added into the lower layer of a well, while cells, $1\times10^4$ cells per well, were added into the upper layer, and those were cultured for 4 hours. Cells were immobilized with methanol and cells in the upper layer of a filter were removed, and cells migrated on the filter were stained with Diff Quick (International Reagents Corp.), then numbers of migrated endothelial cells observed from digital camera image were counted by using Scion Image (Scion Corp.). The statistical analysis was performed as follows: Data were analyzed using Williams' test after linear regression analysis. The difference between test compound groups and non-treated group were considered statistical significant at $P<0.05$.

The results are shown in Table 2. From the results in Table 2, the Test Compound A indicated significantly increased numbers of migration cells with dose dependent manner as compared with those of a non-treated control group, then the Test Compound A was confirmed to promote migration of vascular endothelial cells.

TABLE 2

|  | Concentration (−Log M) | Number | Number of Migration cell |
|---|---|---|---|
| Control |  | 4 | 34 ± 8 |
| Test Compound A | 12 | 4 | 41 ± 8 |
|  | 11 | 4 | 42 ± 6 |
|  | 10 | 4 | 49 ± 6 |
|  | 9 | 4 | 64 ± 8 ** |
|  | 8 | 4 | 64 ± 7 ** |

Values were expressed as the mean ± SE
** $P < 0.01$ vs. control

PHARMACOLOGICAL TEST EXAMPLE 3

Effect of Test Compound A on Luminalization of Vascular Endothelial Cells

The test was conducted according to a report by Yasunaga, C. et al. (Lab Invest, 1989; 61: 698-704). Briefly, human aortic endothelial cells (Cambrex Corp.) were cultured in MCDB131 medium to confluent state. Cells prepared with medium containing the Test Compound A, $5\times10^4$ cells/well, were added on cell matrix gel (Nitta Gelatin Co.) and cultured for 4 hours to adhere cells. After medium removal, gel was added to embed cells, and medium containing the drug was added on the upper layer, then length of the formed tube was measured on the third day based on digital camera image by using Scion Image (Scion Corp.). The statistical analysis was performed as follows: Data were analyzed using Williams' test after linear regression analysis. The difference between test compound groups and non-treated group were considered statistical significant at P<0.05.

The results are shown in Table 3. From the results in Table 3, the Test Compound A indicated significantly increased length of formed tube with dose dependent manner as compared with those of a non-treated control group, and the test compound A was confirmed to promote tube formation of vascular endothelial cells.

TABLE 3

| | Concentration (−Log M) | Number | Length of formed tube (Pixel) |
|---|---|---|---|
| Control | | 4 | 13.3 ± 0.4 |
| Test | 8 | 4 | 15.7 ± 0.9 |
| Compound A | 7 | 4 | 32.2 ± 3.8 ** |
| | 6 | 4 | 48.4 ± 5.3 ** |

Values were expressed as the mean ± SE
** P < 0.01 vs. control

The invention claimed is:

1. A method for promoting angiogenesis, which comprises administering to a person in need of improvement of blood circulation a pharmaceutical composition having, as the active ingredient, at least one compound selected from a group consisting of a piperidine compound represented by the formula (1) or salts thereof:

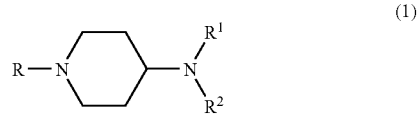

wherein R represents a benzoyl group which may have, as substituents on the phenyl ring, 1 to 3 groups selected from a group consisting of an amino group, which may have a lower alkanoyl group, and a lower alkyl group; $R^1$ represents a hydrogen atom or a lower alkyl group; and $R^2$ represents a phenyl lower alkyl group.

2. The method according to claim 1, wherein the piperidine compound is 4-[N-methyl-N-(2-phenylethyl)amino]-1-(3,5-dimethyl-4-propionylaminobenzoyl)piperidine.

3. The method according to claim 1 or claim 2, wherein the pharmaceutical composition is a therapeutic drug for diseases with insufficient development and regeneration of blood vessels, and diseases caused by ischemia.

4. The method according to claim 3, wherein the diseases with insufficient development and regeneration of blood vessels, and diseases caused by ischemia are selected from the group consisting of myocardial infarction, angina pectoris, cerebral infarction, and senile dementia.

* * * * *

UNITED STATES PATENT AND TRADEMARK OFFICE
CERTIFICATE OF CORRECTION

| | | |
|---|---|---|
| PATENT NO. | : 8,445,516 B2 | Page 1 of 1 |
| APPLICATION NO. | : 10/587045 | |
| DATED | : May 21, 2013 | |
| INVENTOR(S) | : Hashimoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1631 days.

Signed and Sealed this
Seventh Day of April, 2015

Michelle K. Lee
*Director of the United States Patent and Trademark Office*